(12) United States Patent
Ewart et al.

(10) Patent No.: US 7,179,793 B2
(45) Date of Patent: Feb. 20, 2007

(54) ANTI-HYPERTENSIVE DIETARY SUPPLEMENT

(75) Inventors: Harry Stephen Ewart, Halifax (CA); Dorothy Anne Dennis, Halifax (CA); Colin Barrow, Halifax (CA); Michael Anthony Potvin, Dartmouth (CA)

(73) Assignee: Ocean Nutrition Canada Limited, Dartmouth (CA)

( * ) Notice: Subject to any disclaimer, the term of this patent is extended or adjusted under 35 U.S.C. 154(b) by 25 days.

(21) Appl. No.: 11/056,145

(22) Filed: Feb. 14, 2005

(65) Prior Publication Data

US 2006/0183690 A1    Aug. 17, 2006

(51) Int. Cl.
*A61K 38/01* (2006.01)
*A61K 38/06* (2006.01)
*C07K 1/12* (2006.01)
*C07K 5/08* (2006.01)

(52) U.S. Cl. .................. 514/18; 424/439; 426/657; 435/68.1; 514/21; 530/331; 530/343; 530/857

(58) Field of Classification Search .................. None
See application file for complete search history.

(56) References Cited

U.S. PATENT DOCUMENTS

| | | | |
|---|---|---|---|
| 4,584,197 | A | 4/1986 | Takasaki et al. |
| 6,214,797 | B1 | 4/2001 | Vale, Jr. et al. |
| 7,034,002 | B1 * | 4/2006 | Fujita .................. 514/15 |
| 2004/0087504 | A1 | 5/2004 | Osajima et al. |

FOREIGN PATENT DOCUMENTS

| | | | |
|---|---|---|---|
| JP | 05238921 | | 9/1993 |
| JP | 7-188282 | A * | 7/1995 |
| JP | 11-29594 | A * | 2/1999 |
| JP | 11343297 | | 12/1999 |
| JP | 04083529 | | 2/2004 |
| WO | WO 84/01378 | A1 | 4/1984 |
| WO | WO 90/05742 | A1 | 5/1990 |
| WO | WO 01/68115 | A1 | 9/2001 |
| WO | WO 2004/016098 | A1 | 2/2004 |
| WO | WO 2005/002605 | A1 | 1/2005 |

OTHER PUBLICATIONS

Gao et al. Hydrophobic Contributiion Constants . . . Pharmaceutical Research. 1995, vol. 12, No. 9, pp. 1279-1283.*
Yang et al. Isolation and Antihypertensive Effect . . . Journal Of Agricultural And Food Chemistry. 2003, vol. 51, No. 17, pp. 4897-4902.*
Kawasaki, T. et al., "Antihypertensive effect of Valyl-Tyrosine, a short chain peptide derived from sardine muscle hydrolyzate, on mild hypertensive subjects", Journal of Human Hypertension, (2000), p. 519-523, vol. 14, No. 8 (Abstract only).

(Continued)

*Primary Examiner*—Jeffrey Edwin Russel

(57) ABSTRACT

An anti-hypertensive fish protein hydrolysate is provided, wherein the fish is of the genus *Salmo* or *Oncorhynchus*, and wherein the fish protein hydrolysate comprises at least 1 peptide selected from the group consisting of: Leu-Ala-Phe, Leu-Thr-Phe, Ile-Ile-Phe, Leu-Ala-Tyr, Ile-Ala-Tyr, Val-Phe-Tyr, Tyr-Ala-Tyr, Val-Leu-Trp, Ile-Ala-Trp, Tyr-Ala-Leu and Tyr-Asn-Arg. Methods of making and methods for using such fish protein hydrolysates are also provided.

33 Claims, 4 Drawing Sheets

OTHER PUBLICATIONS

Kristinsson, Hordur G. et al., "Fish Protein Hydrolysates: Production, Biochemical, and Functional Properties", Critical Reviews in Food Science and Nutrition, (2000), p. 43-81, vol. 40(1), CRC Press LLC.

Liaset, Bjørn et al., "Chemical composition and theoretical nutritional evaluation of the produced fractions from enzymic hydrolysis of salmon frames with Protamex™", Process Biochemistry, (2003), p. 1747-1759, vol. 38, Elsevier Science Ltd.

Okamoto, Akiko (Kainuma) et al., "Angiotensin I-Converting Enzyme Inhibitory Action of Fish Sauce", Food Sci. Technol. Int., (1995), p. 101-106, vol. 1(2).

Ono, S. et al., "Isolation of Peptides with Angiotensin I-converting Enzyme Inhibitory Effect Derived from Hydrolysate of Upstream Chum Salmon Muscle", Journal of Food Science, (2003), p. 1611-1614, vol. 68, No. 5, Institute of Food Technologists.

Sato, Minoru et al., "Angiotensin I-Converting Enzyme Inhibitory Peptides Derived from Wakame (*Undaria pinnatifida*) and Their Antihypertensive Effect in Spontaneously Hypertensive Rats", J. Agric. Food Chem., (2002), p. 6245-6252, vol. 50, American Chemical Society, published on Web Sep. 14, 2002.

Seki, Eiji et al., "Antihypertensive Effect of Sardine Peptide and Valyl-Tyrosine in Spontaneously Hypertensive Rats", J. Jpn. Soc. Nutr. Food Sci., (1999), p. 271-277, vol. 52 (English Abstract included).

Wergedahl, Hege et al., "Fish Protein Hydrolysate Reduces Plasma Total Cholesterol, Increases the Proportion of HDL Cholesterol, and Lowers Acyl-CoA:Cholesterol Acyltransferase Activity in Liver of Zucker Rats", Fish Protein and Lipid Metabolism, (2004), p. 1320-1327, American Society for Nutritional Sciences.

Kohama Y. et al., "Potent synthetic analogues of angiotensin-converting enzyme inhibitor derived from tuna muscle", Agric. Biol. Chem. 1991, pp. 2169-2170, vol. 55, No. 8.

Kristinsson HG et al., "Fish Protein Hydrolysates: Production, Biochemical, and Functional Properties", Crit. Rev. Food Sci. Nutr., 2000, pp. 43-81, vol. 40, No. 1., CRC Press LLC.

Ohta T. et al., "Antihypertensive Action of the Orally Administered Protease Hydrolysates of Chum Salmon Head and Their Angiotensin I-Converting Enzyme Inhibitory Peptides", Food Sci. Technol. Int. Tokyo, 1997, pp. 339-343, vol. 3, No. 4.

Yamamoto N. et al., "Biogenic Peptides and Their Potential Use", Curr. Pharm. Design, 2003, pp. 1345-1355, vol. 9.

Wergedahl, H., et al., Fish protein hydrolysate reduces plasma total cholesterol, increases the proportion of HDL cholesterol, and Lowers Acyl-CoA:cholesterol acyltransferase activity in liver of zucker rats, J. Nutr., (2004) p. 1320-1327, ISSN:0022-3166, vol. 134.

* cited by examiner

ANTI-HYPERTENSIVE DIETARY SUPPLEMENT

FIELD OF THE INVENTION

The invention concerns an anti-hypertensive composition, a method of producing such composition and a dietary supplement made by way of such a method.

BACKGROUND OF THE INVENTION

Hypertension is a condition commonly associated with narrowing of the arteries. This causes blood to be pumped with excessive force against the artery walls. It is a sign that the heart and blood vessels are being overworked. If left untreated hypertension can cause serious cardiovascular disease. For example, the heart muscle can thicken (cardiac hypertrophy) and function abnormally, or dilate and contract less forcefully (dilated cardiomyopathy). High blood pressure can also cause injury to the brain, the eyes and/or the kidneys. Hypertensive patients are also at increased risk of having a stroke.

In vivo the renin/angiotensin system functions to regulate blood pressure. This system comprises the angiotensin I-converting enzyme (ACE) which catalyses the cleavage of inactive angiotensin I into the active vasoconstrictor, angiotensin II. ACE also catalyses the degradation of the vasodilator, bradykinin.

Various enzymatic hydrolysates and peptides derived from food protein have been reported to have ACE inhibitory activity.

In particular, Ono et al. (2003) report that a chum salmon hydrolysate, obtained using thermolysin, had ACE inhibitory activity. Thermolysin is a metalloendopeptidase with a specificity for peptide bonds on the N-terminal side of hydrophobic amino acids, and which is produced by *Bacillus thermoproteolyticus*).

Ohta et al. (1997) report that a hydrolysate obtained by hydrolysis of a chum salmon head with the commercial serine endopeptidase Biopurase SP10 (from *Bacillus subtilis*) had greater ACE inhibitory activity than hydrolysates prepared by digestion of the salmon head with any of the following commercial proteases: XP-415 (from *Rhizopus delemar*), Papain (from *Carica papaya*), DenazymeAP (from *Aspergillus oryzae*) or Denapsin2P (from *Aspergillus niger*).

However, neither Ono et al. nor Ohta et al. report the use of a bacillolysin in preparing anti-hypertensive fish protein hydrolysates.

SUMMARY OF THE INVENTION

Accordingly, in one aspect the invention provides an anti-hypertensive fish protein hydrolysate, wherein said fish is of the genus *Salmo* or *Oncorhynchus*, and wherein the fish protein hydrolysate comprises at least 1 peptide selected from the group consisting of:

Leu-Ala-Phe, Leu-Thr-Phe, Ile-Ile-Phe, Leu-Ala-Tyr, Ile-Ala-Tyr, Val-Phe-Tyr, Tyr-Ala-Tyr, Val-Leu-Trp, Ile-Ala-Trp, Tyr-Ala-Leu and Tyr-Asn-Arg.

Such hydrolysates may be prepared by hydrolyzing the fish protein with a bacillolysin.

In another aspect, the present invention provides an anti-hypertensive composition comprising an anti-hypertensive fish protein hydrolysate as described above.

In still another aspect, the present invention provides a dietary supplement, nutraceutical product, or functional food product comprising an anti-hypertensive fish protein hydrolysate as described above.

In yet another aspect, the present invention provides a method for treating or preventing hypertension in a patient comprising administering to a patient in need thereof an anti-hypertensive fish protein hydrolysate as described above.

The invention provides, in another aspect, a method for inhibiting angiotension I-converting enzyme (ACE) activity in a patient comprising administering to a patient in need thereof an anti-hypertensive fish protein hydrolysate as described above.

In still another aspect, the present invention provides a method for reducing mean blood pressure comprising administering to a patient in need thereof an anti-hypertensive fish protein hydrolysate.

In still yet another aspect, the present invention provides a method of producing an anti-hypertensive dietary supplement comprising hydrolyzing fish protein with a bacillolysin, wherein said fish is of the genus *Salmo* or *Oncorhynchus*.

In still a further aspect, the present invention provides an anti-hypertensive fish hydrolysate, obtained by or obtainable by the method described above.

DETAILED DESCRIPTION OF THE INVENTION

Fish Species

Figure 1:
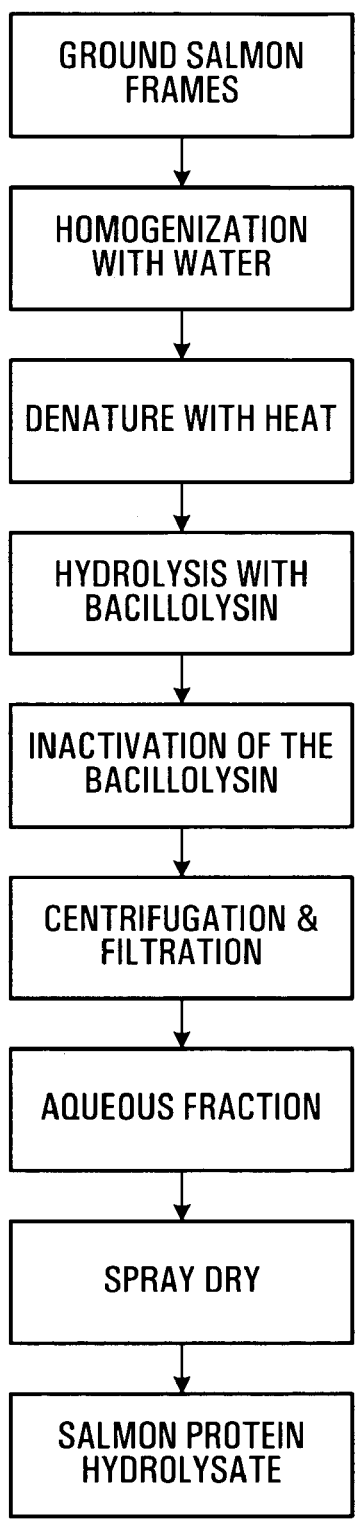
FIG. 1 is a flow chart illustrating steps in the preparation of a salmon protein hydrolysate according to the invention.

The fish species used in accordance with the present invention are of the salmonid type, which includes the genus *Salmo* or *Oncorhynchus*. Most preferably, the fish are selected from the group consisting of: atlantic salmon (*Salmo salar*) also know as kennebec salmon, sebago salmon, grilse or kelt; coho salmon (*Oncorhynchus kisutch*) also known as silver salmon, sea trout or blueback; chinook salmon (*Oncorhynchus tshawytscha*) also known as king salmon, tyee, spring salmon or quinnat; steelhead salmon (*Oncorhynchus mykiss*) also known as rainbow or silver trout; pink salmon (*Oncorhynchus gorbuscha*); and sockeye salmon (*Oncorhynchus nerka*)

The fish used in the invention may comprise the whole fish, a fillet, a rack, other fish parts, extracts or purified or partially purified fish proteins.

Hydrolysates

If the fish protein is initially provided in the form of, for example, a fish fillet, rack or whole fish, the fish material is preferably ground using a grinding machine known to those of skill in the art. The fish may also be de-boned using de-boning apparatus prior to grinding. Alternatively, the starting material may be pre-ground, or take the form of an extract or purified or partially purified fish protein product, in which case further grinding is not required.

The ground fish may be homogenized in water or other aqueous solution in, for example, a 1:1 ratio.

The water or aqueous solution may contain an anti-bacterial agent such as methyl and/or propyl parabens to minimize bacterial degradation. Typically, if both methyl- and propylparabens are added it may be in the ratio, 2 parts methylparabens and 1 part propylparabens. Optionally, a further preservative may be added.

The protein present in the homogenized mixture of water and ground fish may be preferably denatured using heat prior to hydrolysis. The denaturing temperature may be, for example, greater than 65° C. and most preferably, about 70° C.

Preferably, the denaturing step may be from, for example, 5 to 20 minutes in duration. More preferably, the denaturing step may be from 5 to 15 minutes in duration. Most preferably, the denaturing step may be about 10 minutes in duration.

The mixture may preferably be cooled, for example, to about 50° C. and the pH of the mixture adjusted to, for example, between about pH 7 to pH 9 by the drop-wise addition of 1N sodium hydroxide. Preferably, the pH is adjusted to about 8.

Enzymatic hydrolysis is carried out using an enzyme of the metalloendopeptidase type selected from those in the Enzyme Commission class: EC 3.4.24.28, which are also known as bacillolysins. More particularly, the metalloendopeptidase may be selected from those that preferentially catalyse the hydrolysis of peptide bonds on the C-terminal side of, in descending order with the most preferred amino acid first, arginine, alanine, lysine, phenylalanine and leucine.

In one embodiment, the enzyme is a bacillolysin produced by fermentation of *Bacillus stearothermophilus*. A preferred type of bacillolysin is Protease S Amano. Protease S Amano is obtainable from Amano Enzyme USA Company Limited (Lombard, Ill.).

When Protease S Amano is used, it may be added at a ratio of from about 1.6% to 3.6% w/w Protease S Amano to fish protein substrate. For example, the ratio may be from about 2.0% to 3.0% w/w and most preferably about 2.6% w/w.

Hydrolysis of the fish protein may be performed at a temperature of, for example, from about 45° C. to 75° C. Preferably the hydrolysis is carried out at a temperature of from about 45° C. to about 55° C., most preferably at a temperature of about 50° C.

Hydrolysis is preferably carried out until a degree of hydrolysis of about 10% to about 30% is achieved. A degree of about 17% hydrolysis is particularly preferred. Typically this takes from about 3 to about 8 hours to achieve. Preferably the hydrolysis reaction proceeds for about 5.5 to about 7.5 hours. Most preferably the hydrolysis reaction proceeds for about 6.5 to about 7 hours. Advantageously, it is not necessary to constantly maintain a steady pH value of the homogenized fish mixture during the hydrolysis reaction.

If desired, the protein content in the ground fish material may be determined by a method known to those skilled in the art, for example, by the Kjeldahl nitrogen method wherein the percentage protein is equal to the percentage nitrogen multiplied by 6.25. The degree of hydrolysis may be determined by the OPA reaction method.

The homogenized mixture may be heated to a temperature greater than 80° C. for longer than 3 minutes to inactivate the metalloendopeptidase and thereby stop the hydrolysis reaction.

Bones and other, heavy, insoluble material may be removed from the mixture by, for example, filtration through a screen or two-phase centrifugation.

The, light, insoluble fraction and oil may be removed by, for example, three-phase centrifugation or vacuum filtration through a suitable filter or membrane, for example, diatomaceous earth.

The aqueous fraction is preferably dried such as by spray drying to obtain a powdered fish protein hydrolysate.

Alternatively, the aqueous fraction may be concentrated, for example, with a rotary evaporator, and then lyophilized, or spray-dried to yield a concentrated, powdered, protein hydrolysate.

Alternatively, the aqueous fraction may be further processed either before or after concentration and/or freeze-drying by for example, ethanol precipitation, ultrafiltration or reverse-phase chromatography to remove salt, high molecular weight peptides or protein fragments. The aqueous fraction may also be further processed by, for example, filtration, chromatography, dialysis and/or centrifugation, or any combination thereof, as are known in the art.

Advantageously, the fish protein hydrolysate of the present invention is not required to be processed further by, for example, ethanol precipitation, ultrafiltration or reverse-phase chromatography for it to be efficacious.

The fish protein hydrolysate comprises at least one peptide selected from the group consisting of Leu-Ala-Phe, Leu-Thr-Phe, Ile-Ile-Phe, Leu-Ala-Tyr, Ile-Ala-Tyr, Val-Phe-Tyr, Val-Leu-Trp, Ile-Ala-Trp, Tyr-Ala-Leu, and Tyr-Asn-Arg. Of this group Leu-Ala-Phe, Leu-Thr-Phe, Ile-Ile-Phe, Val-Phe-Tyr, Ile-Ala-Trp and Val-Leu-Trp are preferred, and the hydrolysate preferably comprises 1, 2, 3, 4, 5 or all of these peptides. Of this group, Leu-Ala-Phe, Ile-Ile-Phe, Val-Phe-Tyr, Val-Leu-Trp and Ile-Ala-Trp are more preferred, and the hydrolysate preferably comprises 1, 2, 3, 4 or 5 of these peptides. Most preferably, the hydrolysate comprises at least 1, 2, 3, 4, or 5 of the peptides Leu-Ala-Phe, Ile-Ile-Phe, Val-Phe-Tyr, Val-Leu-Trp and Ile-Ala-Trp.

The protein hydrolysate obtained by the methods of the present invention may be used in the production of a composition or compound comprising the above tri-peptides.

Uses

The fish protein hydrolysates of the present invention possess useful anti-hypertensive properties, having been demonstrated to be potent inhibitors of ACE and to reduce mean blood pressure in SHR. Accordingly, the hydrolysates of the invention are useful in the prevention and treatment of hypertension in a subject as well as in the treatment and prevention of the complications of hypertension, for example, cardiac hypertrophy, dilated cardiomyopathy, congestive heart failure, ischaemic heart disease, atherosclerosis, stroke, renal injury including aneurysm, arteriovenous fistula, arterial blockage or renal vein thrombosis; brain damage, loss of vision.

Obesity and diabetes mellitus are conditions in which blood pressure may be elevated. The hydrolysates of the present invention may be of use in the treatment of high blood pressure in these conditions.

The subject may be a mammal, such as a human, companion animal or other mammal of agricultural or commercial importance.

Compositions

Compounds and compositions according to the present invention may be used in a variety of products, for example, pharmaceutical or nutraceutical products, dietary supplements, nutritional supplements, food products, food ingredients and beverages. The fish protein hydrolysate may be microencapulated in order to improve palatability or processing characteristics of the food or beverage products. Alternatively, the fish protein hydrolysates may be used on their own.

Preferably, nutraceutical and pharmaceutical formulations of compositions and compounds in accordance with the present invention are intended for oral administration. The formulations comprise the composition of the present invention in combination with one or more physiologically acceptable ingredients, such as carriers, excipients or diluents. Compositions and formulations for oral administration are particularly preferred. Formulations may be prepared, for example, in unit dose forms, such as hard capsules, tablets, capsules, dragees, and ampoules or as a powder in a sachet for dissolving in a liquid. They may be prepared in a conventional manner, for example by means of conventional mixing, granulating, confectioning, dissolving or lyophilizing processes.

Typical physiologically acceptable ingredients include, for example:
 a) binding agents such as starch, polyvinylpyrrolidone, hydroxypropylmethyl cellulose and/or gelatine;
 b) fillers such as rice powder, sugars (for example, lactose, saccharose, mannitol, sorbitol) and amylopectin, cellulose preparations (for example, microcrystaline cellulose), calcium phosphates (for example, tricalcium phosphate, calcium hydrogen phosphate, lactose), magnesium stearate and/or titanium dioxide;
 c) lubricants such as steric acid, calcium stearate, magnesium stearate, talc, silica, silicic acid, polyethylene glycol and/or waxes;
 d) disintegrants such the above mentioned starches, carboxymethyl starch, cross-linked. polyvinylpyrrolidone, agar, alginic acid or a salt thereof (for example, sodium alginate) and/or sodium starch glycolate;
 e) wetting agents such as sodium lauryl sulphate; and/or
 f) stabilizers.

Soft gelatine capsules may be prepared with capsules containing a mixture of the fish protein hydrolysate composition together with paraffin oil, liquid polyethylene glycols, vegetable oil, fat and/or another suitable vehicle for soft gelatine capsules. Plasticizers such as glycerol or sorbitol may also be used. Hard gelatine capsules may contain granules of the composition. Hard gelatine capsules may also contain the composition in combination with solid powdered ingredients such as those listed above.

Liquid formulations for oral administration may be prepared in the form of solutions, syrups or suspensions. Liquid formulations typically comprise the fish protein hydrolysate composition with an excipient such as sugar or sugar alcohols, and a carrier such as ethanol, water, glycerol, propylene glycol, polyethylene glycol, almond oil, oily esters or mixtures thereof. If desired, such liquid formulations may also contain colouring agents, flavouring agents, saccharine, thickening agents (for example, carboxy methyl cellulose), suspending agents (for example, sorbitol syrup, methylcellulose, hydrogenated edible fats), emulsifying agents (for example, lecithin, acacia), and/or preservatives (for example, methyl p-hydroxy benzoates, propyl p-hydroxy benzoates, sorbic acid). Liquid formulations for oral administration may also be prepared in the form of a dry powder to be reconstituted with water or another suitable vehicle prior to use.

Formulations may contain one or more additional active ingredients particularly one or more further anti-hypertensive agents. The one or more further anti-hypertensive agents is preferably selected from the group consisting of $alpha_1$-adrenergic antagonists, beta-adrenergic antagonists, combined alpha/beta-adrenergic antagonists, adrenergic neuron blocking agents, CNS-acting antihypertensives, angiotensin converting enzyme (ACE) inhibitors, angiotensin-II receptor antagonists, calcium channel blockers and diuretic agents.

An effective amount of the fish protein hydrolysate composition can be determined by the skilled person and may depend on various factors, such as the nature of the product, the condition to be prevented or treated, the method of administration, species of animal, age and/or individual condition. Typically, the dose may comprise between 1 to 5 grams of hydrolysate per day for a 70 Kg human. Preferably the dose comprises 1.5 grams of dry hydrolysate per day. Preferably, the hydrolysate may be taken between 2 to 4 times daily such that the dose does not have to be taken at once.

The following examples are offered by way of illustration and not by way of limitation.

EXAMPLE 1

This example illustrates the preparation and testing of an anti-hypertensive fish protein hydrolysate made using a bacillolysin.

Preparation of ACE Inhibitory Hydrolysate

FIG. 1 outlines the preparation of salmon protein hydrolysate. Ground salmon frames were homogenized with water at a 1:1 ratio. 0.013% parabens (2 parts methyl and 1 part propyl) were added to the water to minimize bacterial degradation. Ground salmon frames were obtained from a salmon processing plant. The mixture was heated to 70° C. and held there for 1omin to denature the protein. The mixture was then cooled to 50° C. After 50° C. was achieved, the pH of the mixture was adjusted to 8.0 with 1N NaOH. Protease S Amano was added at a 2.6% enzyme/substrate (protein) ratio and d at 50° C. for 7 h to a 17.0% degree of hydrolysis. The pH was not maintained constant. Protease S Amano produced by *Bacillus stearothermophilus* fermentation was purchased from Amano Enzyme USA Co., Ltd. (Lombard, Ill.).

Protein content in the ground salmon frames was determined by the Kjeldahl nitrogen method and % protein=% nitrogen×6.25. The protein content in the ground salmon frames was 40%. 70–80% of fish muscle protein is structural protein (actin, myosin, tropomyosin, and actomyosin) and with respect to fish protein hydrolysis is subject to enzymatic hydrolysis. (Kristinsson and Rasco, 2000).

The degree of hydrolysis was determined by the OPA reaction method. Heating the mixture to 85° C. and holding there for 10 min terminated the hydrolysis by inactivating the Protease S Amano. The bones and heavy insoluble fraction were removed by centrifugation. The light insoluble fraction and oil were removed by vacuum filtration through diatomaceous earth. The aqueous fraction was spray dried to obtain a powdered salmon protein hydrolysate. High molecular weight peptides were removed by ethanol precipitation or ultrafiltration.

In vitro ACE Inhibitory Activity

The ACE inhibitory activity ($IC_{50}$) of the salmon protein hydrolysates was determined by the method of Holmquist et al. Table 1 shows the yield, ACE inhibitory activity, molecular weight distribution, and ash content of the hydrolysate without additional processing, and after ethanol precipitation or ultrafiltration. The ACE inhibitory activity of the hydrolysate without additional processing was 58.5 µg/mL. The activities after ethanol precipitation or ultrafiltration were 42.1 µg/mL and 41.1 µg/mL respectively.

TABLE 1

Yield, ACE inhibitory activity, molecular weight distribution, and ash content of salmon protein hydrolysates.

|  | Yield (%) | ACE inhibitory activity (µg/mL) | Average Molecular Weight (daltons) | Ash (%) |
| --- | --- | --- | --- | --- |
| Unprocessed hydrolysate | 6.42 | 58.5 | 1290 | 11.4 |
| Ethanol soluble fraction | n/d | 42.1 | 723 | 15.8 |
| <3000 dalton fraction | 1.02 | 41.1 | 547 | 15.8 |

In-Vivo Antihypertensive Effect in Spontaneous Hypertensive Rats

The antihypertensive effect of a single oral administration of salmon protein hydrolysates in spontaneous hypertensive rats (SHR) was determined. Hydrolysates were unprocessed, and ultrafiltered or ethanol precipitated. Each hydrolysate was dissolved in water and 1500 mg/kg body weight (bw) was administered by gavage. Ultrafiltered Bonito peptide (1307 mg/kg bw to account for its lower ash content) was administered as a positive control. Six rats were included in each treatment group. Mean blood pressure measurements were taken from the carotid artery before, and 1, 2, 4, 6, and 8h after administration.

Figure 2:
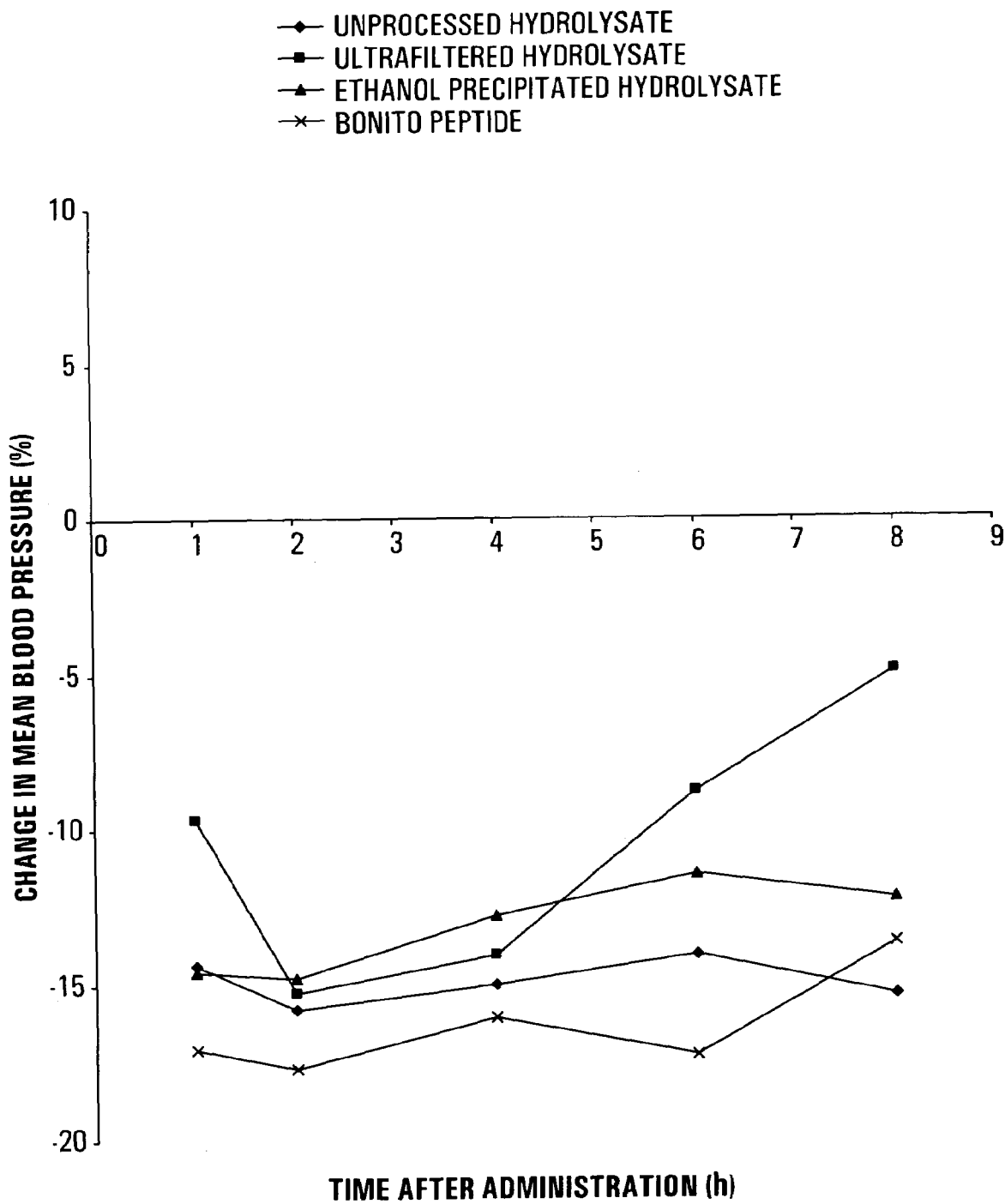
FIG. 2 depicts a graph showing a comparison of the anti-hypertensive effect in spontaneous hypertensive rats of unprocessed, ultrafiltered, and ethanol precipitated Protease S Amano salmon protein hydrolysates. The effect of bonito peptide hydrolysate is depicted for comparison.

The average mean blood pressure was 177±17 mmHg before administration. FIG. 2 shows the changes in mean blood pressure after administration of salmon hydrolysates and bonito peptide in SHR. The in vitro ACE-inhibitory activity of the unprocessed hydrolysate was increased by ultrafiltration or ethanol precipitation. In the SHR, a single oral administration of equal doses of the ultrafiltered and ethanol precipitated hydrolysate and the unprocessed hydrolysate all had significant antihypertensive effects. One hour after administration of the unprocessed hydrolysate and the ethanol-precipitated hydrolysate, the mean blood pressure was significantly reduced by 15% and this reduction was maintained over the 1 to 8 hour measurement period. However, for the ultrafiltered hydrolysate, the mean blood pressure reduction occurred more gradually, becoming evident after 2 h (~15%). This reduction was not prolonged, such that after 4 h blood pressure rose to baseline values.

When the salmon rack is digested with Protease S Amano, the hydrolysate is centrifuged to separate the active peptides (in the supernatant) from debris (for example, bone and undigested protein). This is what is referred to as an "unprocessed" hydrolysate. Based on what is known in the art for other blood pressure lowering hydrolysates the applicants believed that to obtain an efficacious product, a processing step to concentrate the active peptides in the supernatant would be required. For example, the bonito peptide product used as a comparison was processed by an ultrafiltration step (3000 MWCO). This removes high molecular weight peptides. The applicants tested two approaches: ultrafiltration (3000 MWCO) and ethanol precipitation, a step that preferentially removes higher molecular weight peptides. Surprisingly, it was the "unprocessed" hydrolysate that was most effective at reducing blood pressure. In the side-by-side comparison, the unprocessed hydrolysate of the instant invention was as effective at lowering blood pressure as the bonito peptide in vivo.

ACE Inhibitory Peptides

Several ACE inhibitory peptides in the ultrafiltered salmon protein hydrolysate were identified. The ultrafiltered hydrolysate powder in water was applied on a gel filtration TSK-gel G3000PWXL column (7.8×300 mm, 6 µ, Tosoh). The column was eluted with 10% aqueous methanol at a flow rate of 0.8 mL/min. The elution was monitored by UV diode array detection collecting UV absorbance data from 192–450 nm. Individual fractions were lyophilized and their ACE inhibitory activities were measured.

The identification of the peptides in the active fractions and their quantification in the unprocessed hydrolysate was carried out by LC-MS/MS consisting of a Q-Tof detector (Micromass). The peptides were identified by ProteinLynx Global Server software (Micromass). The fractions or standards were applied on a reverse-phase PLRP-S 100A column (4.6×150 mm, 5 µ, Polymer Labs). The column was eluted with a linear gradient of methanol (5–90%/90min.) at a flow rate of 0.2 mL/min.

The ACE inhibitory activity of the ultrafiltered hydrolysate was 41.1 µg/mL. Three fractions A, B, and C) were eluted when the ultrafiltered hydrolysate was fractionated on the gel filtration column. Table 2 shows the yield and ACE inhibitory activity of each fraction. After gel filtration the activity of the most active fraction (C) was 15 µg/mL demonstrating a stronger ACE inhibitory activity in the lower molecular weight fraction. Fraction C was applied to reverse phase HPLC and using the ProteinLynx Global server software, individual peptides were identified. >200 peptides were identified when fraction C was fractionated on the reverse phase column.

Several tripeptides identified in fraction C were synthesized, and their ACE inhibitory activities were determined. Table 1 shows the ACE inhibitory activity of the tripeptides with the most potent ACE inhibitory activity. Tripeptides are considered to be absorbed in their intact form in the intestine without being degraded by gastrointestinal proteases and might have antihypertensive effects in vivo. The ACE inhibitory activities of Leu-Ala-Phe, Leu-Thr-Phe, Ile-Ile-Phe, Leu-Ala-Tyr, Ile-Ala-Tyr, Val-Phe-Tyr, Tyr-Ala-Tyr, Val-Leu-Trp, Ile-Ala-Trp, Tyr-Ala-Leu, and Tyr-Asn-Arg were 13.7, 30.7, 8.9, 32.9, 57.5, 11.1, 13.2, 3.7, 56.2, and 54.8 µg/mL respectively. The identification of each of these peptides was confirmed with the corresponding synthetic peptide by their retention time and mass spectroscopy and the synthetic peptide was used to quantitate each peptide in the unprocessed hydrolysate by LC-MS/MS. Among these peptides, Leu-Ala-Phe, Ile-Ala-Phe, Val-Phe-Tyr, Tyr-Ala-Tyr, Val-Leu-Trp, and Ile-Ala-Trp have been quantitated in the unprocessed hydrolysate. Table 3 also shows the peptides contents in the unprocessed hydrolysate.

TABLE 2

Fractions from Gel Filtration of the ultrafiltered hydrolysate.

| Fraction | Yield (%) | IC$_{50}$ (µg/mL) |
|---|---|---|
| Ultrafiltered hydrolysate | | 58.5 |
| A | 82 | 105.0 |
| B | 15 | 52.1 |
| C | 3 | 16.5 |

TABLE 3

Some tripeptides identified in fraction C.

| Tripeptide | IC$_{50}$ (µg/mL; [µM]) | Content in the unprocessed hydrolysate (µg/g) |
|---|---|---|
| Leu-Ala-Phe | 13.7 [39.2] | ~3.6 |
| Leu-Thr-Phe | ~30.7 | |
| Ile-Ile-Phe | 8.9 [22.7] | ~0.4 |
| Leu-Ala-Tyr* | ~32.9 | |
| Ile-Ala-Tyr* | ~57.5 | |
| Val-Phe-Tyr | 11.1 [26.0] | ~22 |
| Tyr-Ala-Tyr | 13.2 [31.8] | ~0.01 |
| Val-Leu-Trp | 10.0 [24.0] | ~280 |
| Ile-Ala-Trp | 3.7 [9.5] | ~0.5 |
| Tyr-Ala-Leu* | ~56.2 | |
| Tyr-Asn-Arg* | ~54.8 [121] | |

*Semi-pure synthetic peptides.

EXAMPLE 2

This example compares the ACE inhibitory activity of salmon protein hydrolysates prepared using various proteases. Salmon frames were d in optimum hydrolysis conditions with various proteases by the process described in Example 1 and the ACE inhibitory activity of the hydrolysates was determined by the methods described in Example 1.

Figure 3:
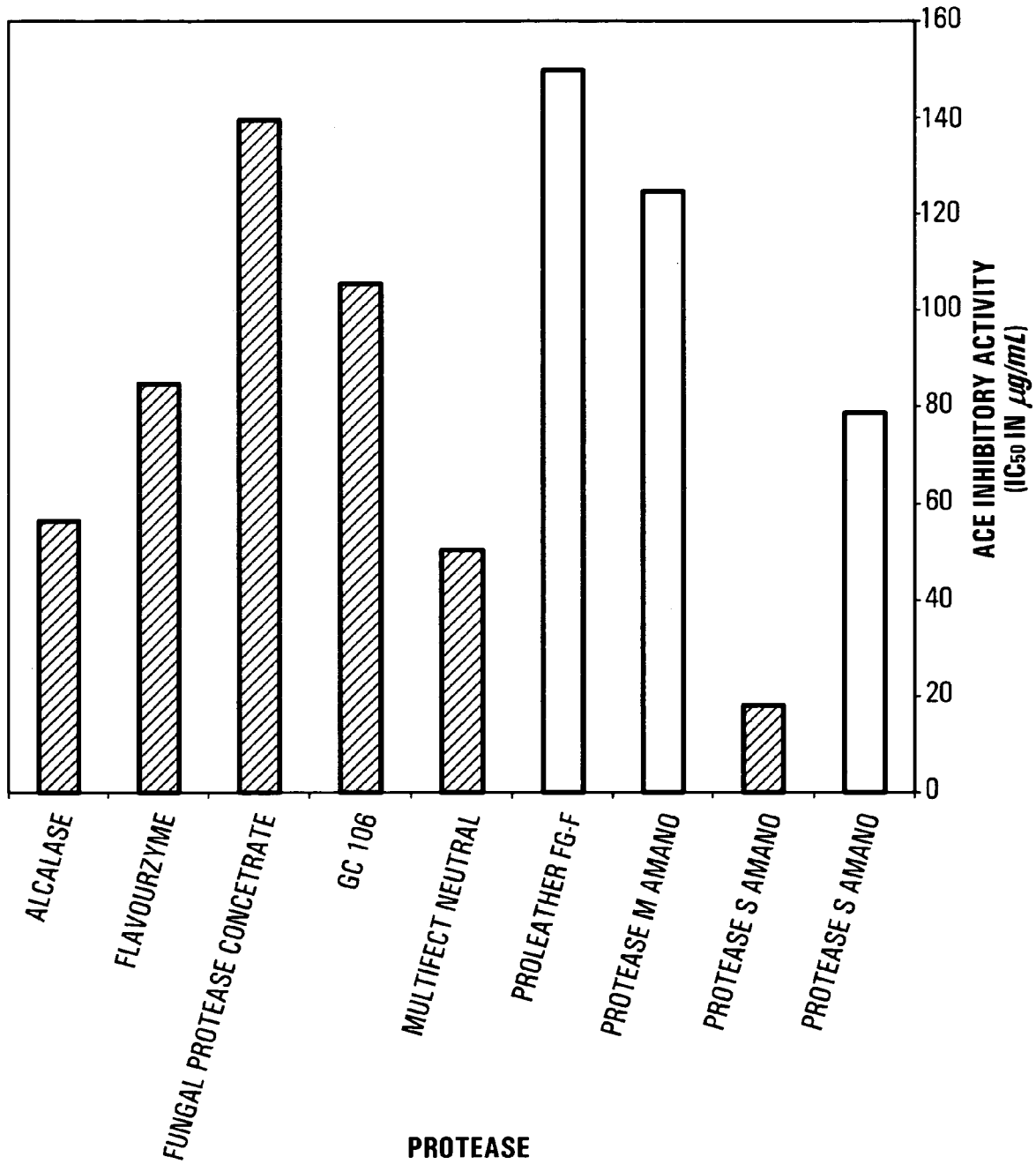
FIG. 3 depicts a graph showing a comparison of ACE inhibitory $IC_{50}$ values of salmon protein hydrolysates obtained using various proteases.

FIG. 3 shows the ACE inhibitory activities of salmon protein hydrolysates obtained using different proteases which had no additional processing or were purified further on a Diaion® HP-20 solid phase column. The proteases were obtained from the following manufacturers: Alcalase (Novozymes); Flavourzyme (Novozymes); Fungal Protease Concentrate (Genencor); GC106 (Genencor); Multifect® Neutral (Genencor); Proleather FG-F (Amano Enzymes) and Protease S Amano (Amano Enzymes).

As can be seen from the FIG. 3, hydrolysates that were obtained by using Protease S Amano and Multifect Neutral proteases, which were subsequently purified on the solid phase column, demonstrated the best in vitro ACE inhibitory activity.

As shown in FIG. 3, the hydrolysates prepared with various proteases differed substantially in ACE inhibitory activity. Without wishing to be bound by any particular theory, it is believed that the differing activity of the various hydrolysates likely results from their differing peptide compositions, resulting from the different specificities of the proteases used to prepare the hydrolysates.

EXAMPLE 3

In this example, the in vivo anti-hypertensive effect of a salmon protein hydrolysate prepared using Protease S Amano is compared to that of a salmon protein hydrolysate prepared using Multifect® Neutral.

The in vivo effect of a single oral administration of 1500 mg/kg of body weight to spontaneous hypertensive rats (SHRs) was determined.

Hydrolysates prepared with Protease S Amano and Multifect® Neutral, using optimal digestive conditions of the enzymes and ethanol precipitated to remove high molecular weight peptides, had IC$_{50}$ of 40.5 µg/mL and 32.8 µg/mL, respectively.

Figure 4:
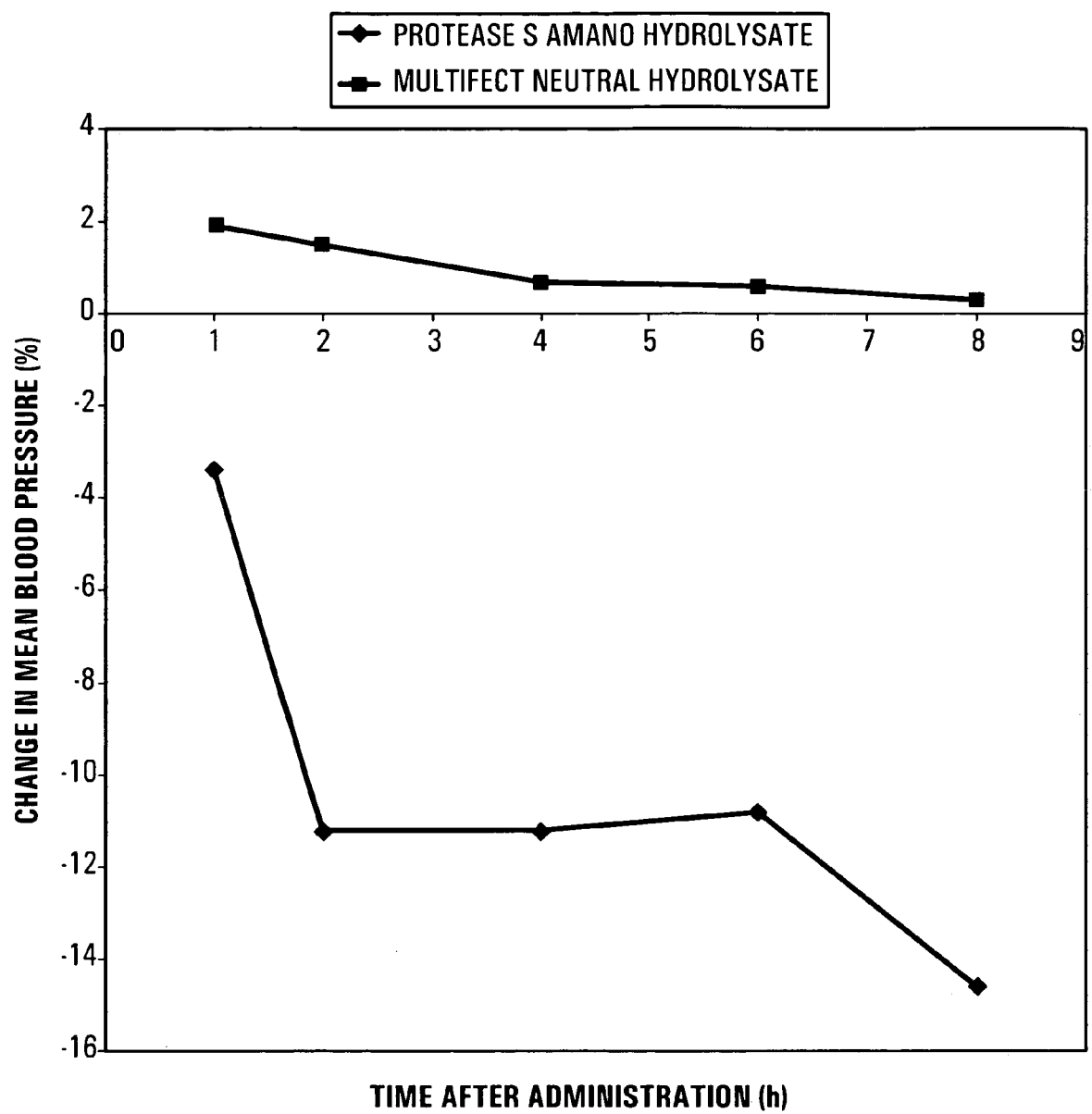
FIG. 4 depicts a graph showing a comparison of the anti-hypertensive effect in spontaneous hypertensive rats of salmon protein hydrolysates prepared with Protease S Amano and Multifect Neutral.

Referring to FIG. 4 it can be seen that only the ethanol precipitated hydrolysate prepared using Protease S Amano resulted in an in vivo reduction in blood pressure. The Protease S Amano hydrolysate significantly reduced mean carotid blood pressure by −11.2% to −14.6% during the period from 2 to 8 hours from administration.

REFERENCES

Holmquist B, Bunning P, Riordan J F. A Continuous Spectrophotometric Assay for Angiotension Converting Enzyme. Analytical Biochemistry 1979;95:540–548.

Kristinsson H, Rasco B. Fish Protein Hydrolysates: Production, Biochemical, and Functional Properties. Critical Reviews in Food Science and Nutrition 2000;40(1):43–81.

Maruyama S, Tanaka H, Maeda H, Miyoshi S, Ishikawa H, Fukui F. Oligopeptide, Angiotension Converting Enzyme Inhibitors, Hypotensive Agent, and Method for Treatment of Hypertension. Patent number 05238921 1993.

Ohta T. et al. Antihypertensive Action of the Orally Administered Protease Hydrolysates of Chum Salmon Head and Their Angiotensin I-Converting Enzyme Inhibitory Peptides. Food Sci. Technol. Int. Tokyo 1997;3(4):339–343.

Ono et al. Isolation of Peptides with Angiotensin I-Converting Enzyme Inhibitory Effect Derived from Hydrolysate of Upstream Chum Salmon Muscle. Journal of Food Science 2003;68(5):1611–1614.

Yasuda M, Izeki T, Sezoko M, Kaneshiro M. Blood Pressure Suppressant Using Red Koji Yeast, and Production Method Therefor. Publication number 04083529 JP 2004.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The invention claimed is:

1. An anti-hypertensive fish protein hydrolysate, wherein said fish is of the *Salmo spp.* or *Oncorhynchus spp.* type, and wherein the fish protein hydrolysate comprises at least 2 peptides selected from the group consisting of: Leu-Ala-Phe, Leu-Thr-Phe, Ile-Ile-Phe, Val-Phe-Tyr, Ile-Ala-Trp and Val-Leu-Trp.

2. The anti-hypertensive fish protein hydrolysate according to claim 1, comprising at least 3 of the peptides selected from the group defined in claim 1.

3. The anti-hypertensive fish protein hydrolysate according to claim 1, comprising at least 4 of the peptides selected from the group defined in claim 1.

4. The anti-hypertensive fish protein hydrolysate according to claim 1, comprising at least 5 of the peptides selected from the group defined in claim 1.

5. The anti-hypertensive fish protein hydrolysate according to claim 1, comprising the peptides Leu-Ala-Phe, Ile-Ile-Phe, Val-Phe-Tyr, Val-Leu-Trp and Ile-Ala-Trp.

6. The anti-hypertensive fish protein hydrolysate according to claim 1, wherein the fish is selected from the group consisting of: atlantic salmon (*Salmo salar*), Coho salmon (*Oncorhynchus kisutch*), chinook salmon (*Oncorhynchus tshawytscha*), steelhead salmon (*Oncorhynchus mykiss*), pink salmon (*Oncorhynchus gorbuscha*), and sockeye salmon (*Oncorhynchus nerka*).

7. The anti-hypertensive fish protein hydrolysate according to claim 1, produced by the hydrolysis of the fish protein with a bacillolysin.

8. The anti-hypertensive fish protein hydrolysate according to claim 7, wherein the bacillolysin catalyzes the hydrolysis of peptide bonds on the C-terminal side of, in descending order with the most preferred amino acid first, arginine, alanine, lysine, phenylalanine and leucine.

9. The anti-hypertensive fish protein hydrolysate according to claim 7, wherein the bacillolysin is produced by fermentation of *Bacillus stearothermophilus*.

10. The anti-hypertensive fish protein hydrolysate according to claim 7, wherein the bacillolysin is Protease S Amano.

11. An anti-hypertensive composition comprising an anti-hypertensive fish protein hydrolysate according to claim 1.

12. The anti-hypertensive composition according to claim 11, wherein the composition comprises one or more further anti-hypertensive agents.

13. The anti-hypertensive composition according to claim 12, wherein the further anti-hypertensive agents are selected from the group consisting of alpha$_1$-adrenergic antagonists, beta-adrenergic antagonists, combined alpha/beta-adrenergic antagonists, adrenergic neuron blocking agents, CNS-acting anti-hypertensives, angiotensin converting enzyme (ACE) inhibitors, angiotensin-II receptor antagonists, calcium channel blockers and diuretic agents.

14. A dietary supplement, nutraceutical product, or functional food product comprising an anti-hypertensive fish protein hydrolysate according to claim 1.

15. A method for treating or preventing hypertension in a patient comprising administering to a patient in need thereof an anti-hypertensive fish protein hydrolysate according to claim 1.

16. A method for inhibiting angiotension I-converting enzyme (ACE) activity in a patient comprising administering to a patient in need thereof an anti-hypertensive fish protein hydrolysate according to claim 1.

17. A method for reducing mean blood pressure comprising administering to a patient in need thereof an anti-hypertensive fish protein hydrolysate according to claim 1.

18. A method of producing an anti-hypertensive dietary supplement comprising hydrolyzing fish protein with a bacillolysin, wherein said fish is of the genus *Salmo* or *Oncorhynchus*.

19. The method according to claim 18, wherein the fish is selected from the group consisting of: atlantic salmon (*Salmo salar*), coho Salmon (*Oncorhynchus kisutch*), chinook salmon (*Oncorhynchus tshawytscha*), steelhead salmon (*Oncorhynchus mykiss*), pink salmon (*Oncorhynchus gorbuscha*), and sockeye salmon (*Oncorhynchus nerka*).

20. The method according to claim 18, wherein the bacillolysin preferentially catalyzes the hydrolysis of peptide bonds on the C-terminal side of, in descending order with the most preferred amino acid first, arginine, alanine, lysine, phenylalanine and leucine.

21. The method according to claim 18, wherein the bacillolysin is produced by fermentation of *Bacillus stearothermophilus*.

22. The method according to claim 18, wherein the bacillolysin is Protease S Amano.

23. The method according to claim 18, wherein the fish protein is provided in the form of a fish fillet, a fish rack, a whole fish, other fish parts, an extract or purified or partially purified fish proteins.

24. The method according to claim 18, wherein a fish fillet, a fish rack, a whole fish, or other fish part, is subjected to a grinding step.

25. The method according to claim 24, in which ground fish obtained from the grinding step is homogenized in water.

26. The method according to claim 18, comprising the step of denaturing the fish protein using heat prior to hydrolysis with the bacillolysin.

27. The method according to claim 26, in which the denaturing step is at a temperature of from about 65° C. to about 80° C.

28. The method as claimed in claim 27, in which the denaturing step is at a temperature of about 70° C.

29. The method according to claim 18, comprising the step of inactivating the bacillolysin after hydrolysis of the fish protein.

30. The method according to claim 18, comprising the step of centrifuging the hydrolyzed protein to obtain an aqueous fraction.

31. The method according to claim 30, further comprising the step of filtering the hydrolyzed protein to obtain an aqueous fraction.

32. The method according to claim 30, comprising the step of drying the aqueous fraction to obtain a protein hydrolysate.

33. The method according to claim 32, which method comprises the step of spray drying the aqueous fraction.

* * * * *